United States Patent [19]
Quinn

[11] Patent Number: 6,036,673
[45] Date of Patent: Mar. 14, 2000

[54] BOLSTER FOR CORPOREAL ACCESS TUBE ASSEMBLY

[75] Inventor: David G. Quinn, Grayslake, Ill.

[73] Assignee: C. R. Bard, Inc., Murray Hill, N.J.

[21] Appl. No.: 09/204,663

[22] Filed: Dec. 2, 1998

Related U.S. Application Data

[60] Continuation-in-part of application No. 08/847,193, May 1, 1997, Pat. No. 5,860,960, which is a division of application No. 08/734,630, Oct. 18, 1996, Pat. No. 5,860,952, which is a continuation-in-part of application No. 08/583,930, Jan. 11, 1996, abandoned.

[51] Int. Cl.$^7$ ........................................ A61M 5/32
[52] U.S. Cl. ............................. 604/178; 604/174
[58] Field of Search .................... 604/174, 175, 604/177–179, 534, 535, 539

[56] References Cited

U.S. PATENT DOCUMENTS

| | | |
|---|---|---|
| 3,915,171 | 10/1975 | Shermeta . |
| 4,261,363 | 4/1981 | Russo . |
| 4,356,824 | 11/1982 | Vazquez . |
| 4,419,094 | 12/1983 | Patel . |
| 4,435,174 | 3/1984 | Redmond et al. . |

(List continued on next page.)

FOREIGN PATENT DOCUMENTS 0 574 961 A1  12/1993  European Pat. Off. .

OTHER PUBLICATIONS

Brochure entitled, "AMT Presents a Giant Step Forward in Innovation the One Step Button," 1 page, published by Applied Medical Technology, Inc., undated.
Brochure entitled, "Innovation is Back, AMT Presents . . . P.R.G.® Gastrostomy Feeding Systems," 1 page, published by Applied Medical Technology, undated.
Brochure entitled, "Stellar Performance," 2 pages, undated.
Brochure entitled, "Polyurethane, Collapsibility, Locking Systems, Flexible Systems," 2 pages, undated.
Brochure entitled, "Introducing EntriStar™ Single Pass P.E.G./J," 3 pages, published by Sherwood Medical, undated.
Brochure entitled, "Bard® Silicone PEGs, Bard® Guidewire System &Ponsky™ "Pull" PEG," 1 page, published by Bard, undated.
Brochure entitled, "FLEXIFLO® New Inverta–PEG™ Gastrostomy Kit with Roll–Tip Bumper," 2 pages, published by Ross Products Division, Abbott Laboratories, undated.
Brochure entitled, "MIC Gastrostomy Tube," 3 pages, undated.
"AMT . . . The Leader in Innovative Gastrostomy Feeding Systems" (1 page), undated.
"The AMT Button" (1 page), undated.
"Care Giver Guide For The Corpak Button" (1 page), undated.
"For the past seven years, we've proved that keeping a low profile can held you come out on top." (1 page), undated.
"MIC–KEY Feeding Kit" (2 pages), undated.
"The Medical Innovator™ Presents: Pee Wee™ A Low Profile Gastrostomy Feeding Kit" (2 pages), undated.
"Comparing Low–Profile Gastrostomy Tubes" (3 pages), Dec. 1991.
"Incomparable Moss® Tubes . . ." (1 page), undated.
"Moss Decompression—Feeding Catheters" (1 page), undated.

*Primary Examiner*—Corrine McDermott
*Attorney, Agent, or Firm*—Richard G. Lione; Brinks Hofer Gilson & Lione

[57] ABSTRACT

A retention bolster for a flexible tube segment in a corporeal access tube assembly. The bolster includes a body molded in one piece of silicone rubber and cut into two legs along a portion of its length. One of the legs has a collar formed on its free end, with a lip under which the free end of the other leg nestles. To hold the legs together and grip a tube segment between them, an O-ring is rolled over the collar into a depression encircling both legs without contracting into the cut between the legs.

6 Claims, 3 Drawing Sheets

U.S. PATENT DOCUMENTS

| | | |
|---|---|---|
| 4,533,349 | 8/1985 | Bark . |
| 4,543,089 | 9/1985 | Moss . |
| 4,576,603 | 3/1986 | Moss . |
| 4,594,074 | 6/1986 | Andersen et al. . |
| 4,642,092 | 2/1987 | Moss . |
| 4,645,492 | 2/1987 | Weeks . |
| 4,666,433 | 5/1987 | Parks . |
| 4,685,901 | 8/1987 | Parks . |
| 4,699,616 | 10/1987 | Nowak et al. . |
| 4,701,163 | 10/1987 | Parks . |
| 4,717,385 | 1/1988 | Cameron et al. . |
| 4,795,430 | 1/1989 | Quinn et al. . |
| 4,798,592 | 1/1989 | Parks . |
| 4,834,712 | 5/1989 | Quinn et al. . |
| 4,900,306 | 2/1990 | Quinn et al. . |
| 4,932,943 | 6/1990 | Nowak . |
| 4,981,471 | 1/1991 | Quinn et al. . |
| 4,986,815 | 1/1991 | Schneider . |
| 5,073,166 | 12/1991 | Parks et al. . |
| 5,073,170 | 12/1991 | Schneider . |
| 5,125,897 | 6/1992 | Quinn et al. . |
| 5,267,967 | 12/1993 | Schneider . |
| 5,267,969 | 12/1993 | Hirsch et al. . |
| 5,308,325 | 5/1994 | Quinn et al. . |
| 5,342,321 | 8/1994 | Potter . |
| 5,370,625 | 12/1994 | Shichman . |
| 5,374,254 | 12/1994 | Buma . |
| 5,439,444 | 8/1995 | Andersen et al. . |
| 5,451,212 | 9/1995 | Andersen . |
| 5,484,420 | 1/1996 | Russo . |
| 5,690,616 | 11/1997 | Mogg . |

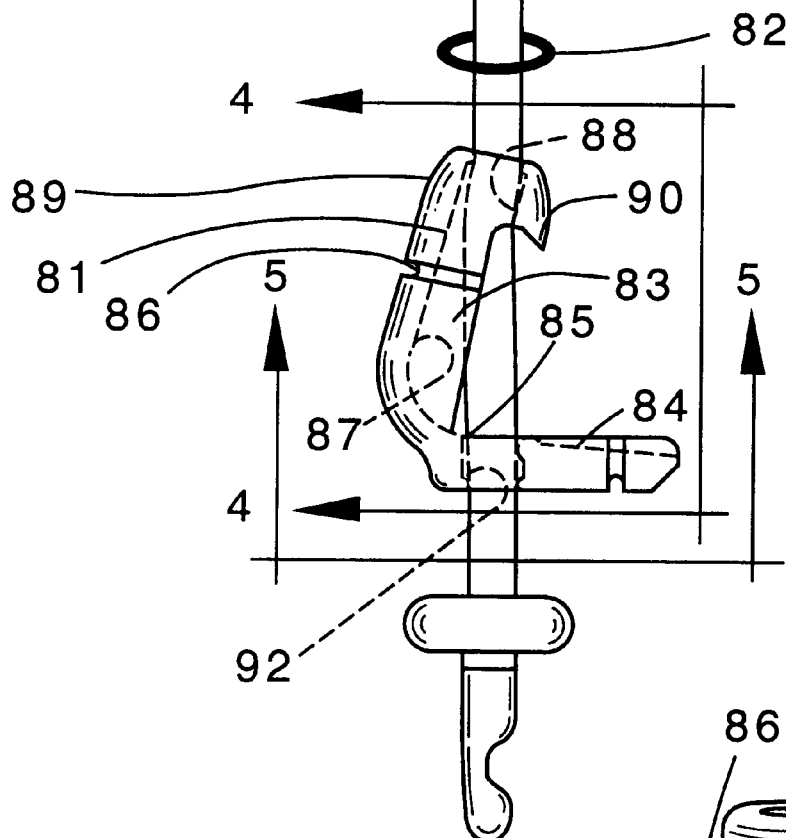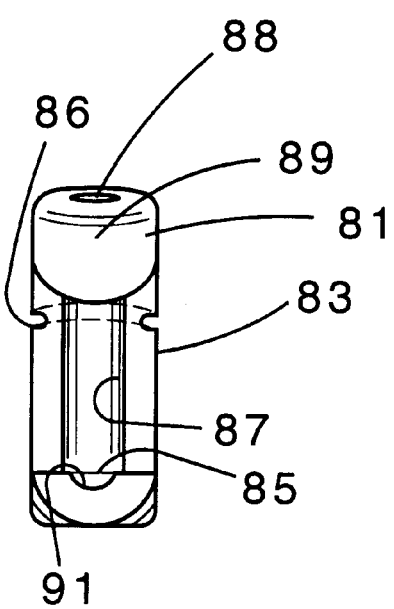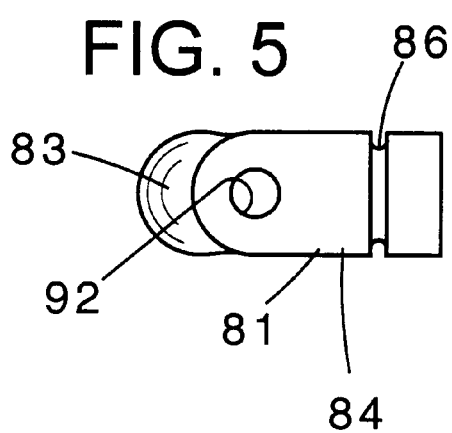

BOLSTER FOR CORPOREAL ACCESS TUBE ASSEMBLY

RELATED APPLICATION

This application is a continuation-in-part of application Ser. No. 08/847,193, filed May 1, 1997, now U.S. Pat. No. 5,860,960 and entitled Improvement In Bolster For Corporeal Access Tube Assembly, which is a division of application Ser. No. 08/734,630, filed Oct. 18, 1996, now U.S. Pat. No. 5,860,952 entitled Corporeal Access Tube Assembly and Method which, in turn, is a continuation-in-part of application Ser. No. 08/583,930, filed Jan. 11, 1996, now abandoned entitled Replacement Gastrotomy Tube.

FIELD OF THE INVENTION

This invention relates generally to medical catheters. It relates particularly to catheters used to access the stomach and/or intestine, or the bladder, through a stoma or ostomy in the abdominal wall.

BACKGROUND OF THE INVENTIONS

The need to artificially introduce food into the gastrointestinal tracts of individuals who can not eat, or will not eat, has been well-known throughout and even prior to this century. Before the mid-1070's, feeding was done nasogastrically with red rubber or polyvinylchloride feeding tubes. The use of enteral feeding by means of nasogastric tubes expanded dramatically in the late 1970's with the introduction of tubes constructed of either silicone rubber or polyurethane. Being constructed of stronger materials, these tubes incorporated thinner walls, and were therefore smaller in outside diameter. These smaller tubes were easier to insert and more comfortable for the patient, and their introduction resulted in a very rapid growth of enteral nutrition via the nasogastric route, and increased interest in enteral nutrition in general.

By the 1980's problems with nasogastric feeding were recognized by clinicians and the advantages of direct gastrostomy access into the stomach through the abdominal wall had been described by Vazquez in U.S. Pat. No. 4,356,824, and by Moss in U.S. Pat. No. 4,543,085. Refinements in securing gastrostomy tubes in the patient were described by Parks in U.S. Pat. No. 4,666,433 and in U.S. Pat. No. 4,685,901.

The 1980's also saw the refinement of methods for forming the gastrostomy stoma. Prior to the 1980's, the stoma or gastrostomy was formed surgically by the Stamm procedure, which required a surgical laporatoratomy to insert the tube, usually a latex urologic Foley retention catheter. A new method, called a "PEG", or Percutaneous Endoscopic Gastrostomy, eliminated the need for a surgical gastrostomy to place the gastrostomy tube and dramatically expanded the interest in the use of direct gastrostomy tubes. The advantages of PEGs and the PEG technique were described by Quinn et al. in U.S. Pat. No. 4,795,430. The word "PEG" is used herein to identify both the tube and the procedure.

Gastrostomy tubes can generally be organized into three main groups, the third of which includes two subgroups:

1. SPECIALTY TUBES placed at the time of gastric surgery by the Stamm technique. The Moss and Vazquez patent tubes are examples of this type.
2. PEG TUBES which are used to form the initial stoma or gastrostomy.
3. REPLACEMENT TUBES which are used to replace PEG TUBES after a period of time because a PEG TUBE has worn out with use, or because a device which is more specific to the patient's need is required. These tubes are inserted into the original stoma created by either the PEG TUBE or the Stamm technique.
   a. LOW PROFILE REPLACEMENT TUBES which are preferred for active patients who wish to conceal the tube's outer fitments during periods when they are not receiving feeding formula. The background for this type of replacement tube is described by Quinn et al. in U.S. Pat. No. 5,125,897.
   b. SIMPLE REPLACEMENT tubes which are less complicated and less expensive are used for patients who are not active and have no need to hide their device. These devices are direct modifications of the original urologic Foley catheters used in early gastrostomies. They are described by Parks in U.S. Pat. No. 4,666,433.

With some exceptions within individual designs, gastrostomy tubes or tube assemblies of the aforedescribed types each incorporate the following seven features or components:

1. A tube to carry the enteral feeding formula into the stomach and or the intestine.
2. An outflow port in the distal end of the tube. The port or ports may be incorporated in the end or the sidewall of the tube. They may also be incorporated in a separate, molded bolus fastened to the distal end of the tube.
3. An administration set connector attached to the proximal end of the tube, which is outside of the patient.
4. A distal end retention device or internal bolster to hold the tube in the stomach, e.g., an inflatable balloon or a molded retention shape which can be deformed with a stylet for insertion and removal.
5. An external bolster to secure the tube at the point where it exits the skin. This bolster maintains the proper distance between the external bolster and the internal retention device, a distance corresponding to the combined thickness of the individual patient's skin, abdominal wall and stomach wall at the site of the gastrostomy.
6. An anti-reflux valve to prevent leakage of gastric acids from the patient when the administration set is being changed or when violent coughing causes excessive back pressure.
7. A measurement system to measure the patient's abdominal wall thickness so that the tube length between the retention device and the external bolster can be adjusted to match this thickness.

In addition to gastrostomy, tubes or tube assemblies of this type are used to administer drugs to, or drain urine from, the bladder. Such tubes or tube assemblies are referred to as suprapubic catheters and comprise the same seven features or components referred to above in the context of gastronomy tubes or tube assemblies. However, they access the bladder through a stoma formed in the abdominal wall above the bladder or pubic area.

The present invention is generally concerned with the external bolster. It is specifically concerned with the clinical use of external bolsters.

SUMMARY OF THE INVENTION

It is an object of the present invention to provide an improved external bolster for a corporeal access tube assembly.

It is another object to provide an external bolster which facilitates installation of a corporeal access tube assembly in a stoma.

It is a further object to provide an external bolster which is maintained in its operational configuration by an easily installed rubber O-ring.

The foregoing and other objects are realized in accord with the invention by providing a molded rubber bolster with an L-shaped passage extending therethrough for receiving a flexible tube segment. The bolster is cut transversely and then longitudinally, from adjacent one end toward the other end, to form mating legs which remain joined at the other end. The legs are separated to permit threading of the tube segment through the passage. The legs are then brought together to bend the tube segment at approximately a right angle and grip the tube segment in this shape. A rubber O-ring is then rolled over the end of the bolster to an annular depression, in which it seats and remains to hold the legs together. The transverse cut between the legs is orientated so that the O-ring cannot inadvertently contract radially into the cut.

BRIEF DESCRIPTION OF THE DRAWINGS

The foregoing and other objects of these inventions are illustrated more or less diagrammatically in the drawings, in which:

FIG. 3 is a side elevational view of the replacement tube assembly seen in FIGS. 1 and 2, illustrated in its unassembled form with the external bolster open prior to insertion of the tube segment, bolus and internal balloon bolster through a stoma formed in a patient's stomach;

FIG. 4 is a front elevational view of the external bolster for the replacement tube assembly of FIG. 3, taken along line 4—4 of FIG. 3, with the other components removed;

FIG. 5 is a bottom plan view of the bolster component of FIG. 4, taken along line 5—5 of FIG. 3, with the other components removed.

DETAILED DESCRIPTION OF THE INVENTION

Figure 1:
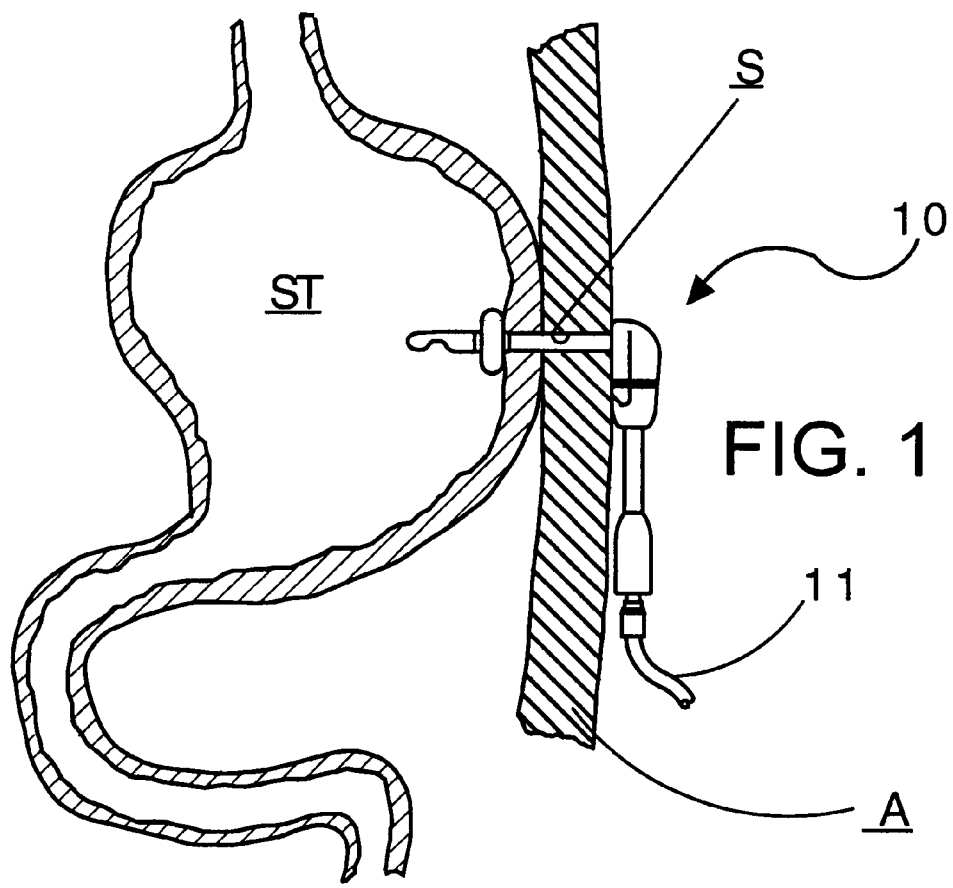
FIG. 1 is an illustration of a replacement tube assembly incorporating an external bolster embodying features of the inventions, with the tube assembly in place accessing a patient's stomach.

Referring now to the drawings, and particularly to FIG. 1, a replacement gastrostomy tube assembly is shown generally at 10. The tube assembly 10 is shown here in place, extending through a stoma S in the patient from a feeding formula supply tube 11 outside the patient's abdominal wall A to inside the patient's stomach ST. The stoma S may be formed in a conventional manner by one of the several well-known procedures hereinbefore referred to.

The tube assembly 10 is a replacement tube assembly in the sense that has also hereinbefore been described. The tube assembly 10 is designed to be easily connected to, and disconnected from, a conventional feeding formula supply tube 11 in a manner hereinafter discussed.

Figure 2:
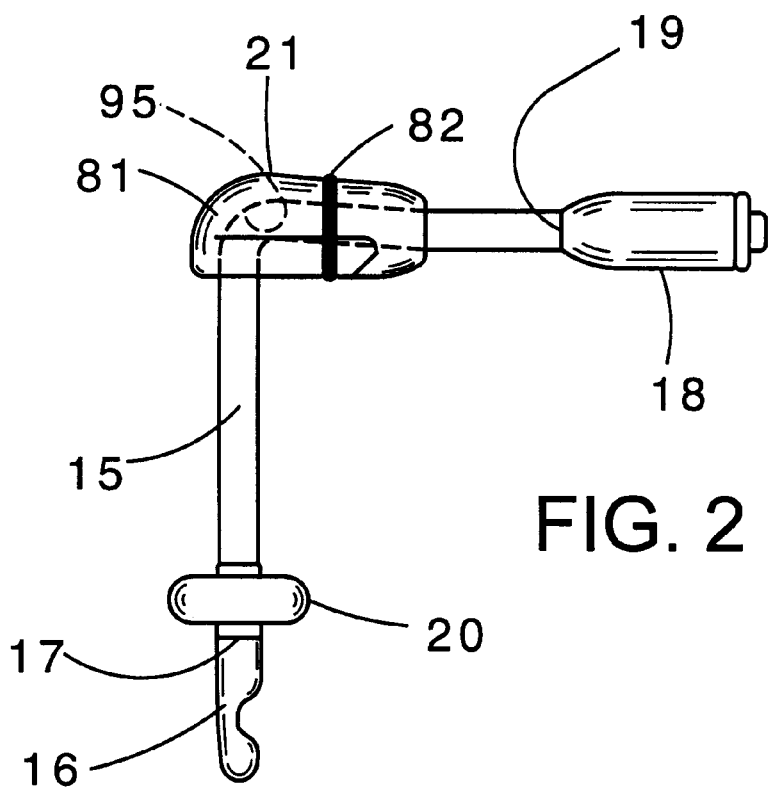
FIG. 2 is an enlarged side elevational view of the replacement tube assembly illustrated in FIG. 1.

Referring now to FIG. 2, the replacement gastrostomy tube assembly 10 is seen to comprise a short segment 15 of tube formed of silicone rubber and embodying features of the invention. The gastrostomy tube segment 15, which is constructed in a manner hereinafter discussed in detail, has a bolus 16 connected in fluid communication with the tube segment at the discharge end 17 of the tube segment, and a set connector 18 connected in fluid communication with the tube segment at its inlet end 19. The bolus 16 and the set connector 18 are also formed of silicone rubber.

Adjacent the bolus tip 16, and encircling the tube segment 15 near the discharge end 17, is a tire-shaped balloon 20. The balloon 20 is preformed in this shape as an internal retention bolster. The preformed balloon 20 is filled with air at ambient pressure to support the balloon in its preformed configuration.

Approximately intermediate the ends 17 and 19 of the tube segment 15 is an external bolster 21 through which the tube segment passes. The bolster 21, which embodies features of the present invention, grips the tube segment 15 at a selected distance from the balloon 20 and forces the tube segment to bend so that the set connector 18 lies immediately adjacent the patient's abdomen when in place.

Referring now also to FIG. 3, the bolster 21 comprises a molded silicone rubber body 81 and a molded silicone rubber O-ring 82. The bolster body 81 is formed in a split configuration so as to have two legs, 83 and 84, joined at corresponding one ends by a bridge 85. The legs 83 and 84 may be spread to the position shown so that the tube segment 15 is essentially straight. In this position, the O-ring 82 is positioned off the bolster 21, freely encircling the tube segment 15. The tube segment 15 is threaded through the bolster 21 and the O-ring 82 placed over it before the set connector 18 is attached, of course.

When the legs 83 and 84 are brought together to the position seen in FIG. 2, the tube segment 15 is bent slightly past a right angle configuration, i.e., the angle is slightly less than 90°, whereby the tube segment outside the bolster is actually inclined slightly toward the abdominal wall. In this position of the legs 83 and 84, the O-ring 82 is rolled over the end of the bolster 21 and snapped into place in an annular depression 86 to maintain the bolster and the tube segment 15 is this position.

Referring additionally to FIGS. 4 and 5, the leg 83 is formed with a substantially semi-cylindrical trough 87 extending axially along one side of it. The trough 87 curves outwardly to terminate at one end at the bridge 85. At its outer end, the trough 87 becomes a cylindrical passage section 88 as it passes through an annular collar 89 which forms what may be referred to as a foot on the leg 83. The other leg 84 is also formed with a substantially semi-cylindrical trough 91 extending axially along one side of it. The trough 91 also curves outwardly to terminate at one end at the bridge 85. Immediately adjacent this curve, a cylindrical passage section 92 is formed through the leg 84, perpendicular to the trough 91.

Figure 6:
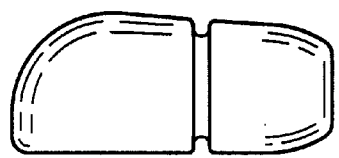
FIG. 6 is a side elevational view of a partially formed bolster.
Figure 7:
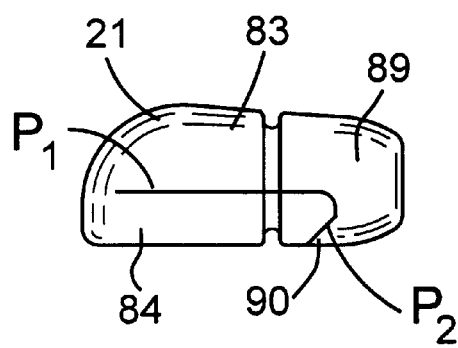
FIG. 7 is a side elevational view of a completed bolster.

Referring now to FIGS. 6 and 7, the bolster 21 is fabricated by molding it in a body 81 without legs (as seen in FIG. 6). The legs 83 and 84 are then formed by cutting through the body 81 on two planes $P_1$ and $P_2$ which follow a generally L-shaped path, as seen in FIG. 7.

The cut between the legs 83 and 84 is planar as it proceeds longitudinally of legs along plane $P_1$. The cut then curves back and extends transversely of the legs 83 and 84 in plane $P_2$, at an angle of 45 to plane $P_1$. This forms the collar 89 with an inclined lip 90 under which the free end of the leg 84 nestles.

It will thus be seen that the normal state of the body 81 is with the legs 83 and 84 lying flush against each other. In this relationship, the two troughs 87 and 91, and the two passage sections 88 and 92, collectively form a generally L-shaped passage 95 extending entirely through the bolster, with the passage section 88 inclined slightly past a right angle. The leg 84 and, thus, the body 81 has a flat bottom surface.

The tube segment 15 is threaded through the passage section 88 in the leg 83 and the passage section 92 in the leg 84 while the legs are spread into the attitude seen in FIGS. 3–5. When the legs 83 and 84 are brought together, the free end of the leg 84 snaps under the lip 90.

Figure 8:
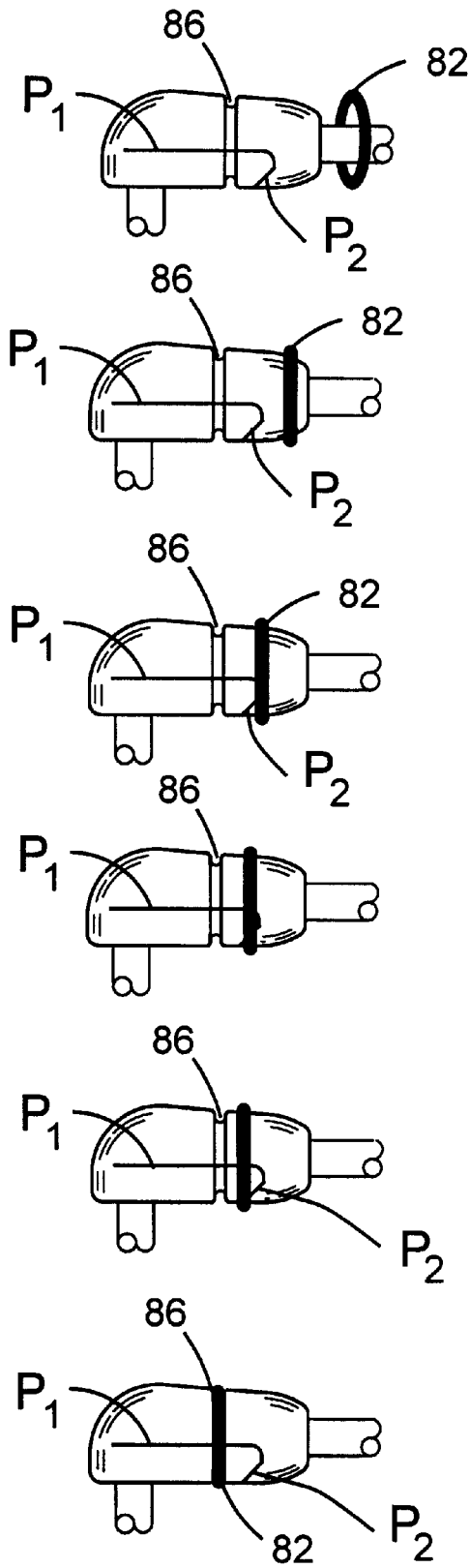
FIG. 8 is an illustration of a six-stage sequence in the bolster assembly.

Referring now to FIG. 8, the O-ring 82 is then rolled over the annular collar 89, as illustrated sequentially. Because the plane $P_2$ is inclined 45° in the direction which the O-ring is rolling, the O-ring (which is radially distended at this stage) does not contract radially into the cut. This facilitates seating of the O-ring in the annular depression 86. As a result, the clinicians task is made easier.

The inventions have been illustrated here in a gastrostomy tube assembly. However, the inventions may find equally advantageous application in other tube assemblies, such as PEG and jejunostomy tubes, for example, or other corporeal access environments like suprapubic catheter assemblies.

While a preferred embodiment of the invention has been described, it should be understood that the invention is not so limited and modifications may be made without departing from the invention. The scope of the invention is defined by the appended claims, and all devices that come within the meaning of the claims, either literally or by equivalence, are intended to be embraced therein.

I claim:

1. A retention bolster for a corporeal access tube assembly wherein said tube assembly includes a flexible tube segment, comprising:
   a) an elongated body molded of rubberlike material;
   b) said body having a passage therein extending substantially along the length of said body and adapted to receive the tube segment;
   c) said body being split along at least a substantial portion of its length to form a pair of legs which are joined together at corresponding one ends by a bridge and are separable at corresponding other ends;
   d) one of said legs having an annular collar formed therein adjacent its other end, said annular collar including a lip under which said other end of the other of said legs is nested;
   e) said body having an annular depression formed around it for receiving an O-ring; and
   f) a removable O-ring adapted to seat in said depression and normally hold said legs flush against each other in order to retain a tube segment in said passage.

2. The retention bolster of claim 1 further characterized in that:
   a) said pair of legs includes an upper leg and a lower leg;
   b) said upper leg having said annular collar.

3. The retention bolster of claim 2 further characterized in that:
   a) said body is molded in one piece of silicone rubber and is split into said pair of legs after being molded.

4. The retention bolster of claim 2 further characterized in that:
   a) said body is split along one plane extending longitudinally of said body and another plane extending transversely of said one plane at an acute angle to said one plane.

5. The retention bolster of claim 4 further characterized in that:
   a) said other plane is disposed at about a 45° angle to said one plane.

6. A retention bolster for a corporeal access tube assembly wherein said tube assembly includes a flexible tube segment, comprising:
   a) an elongated body molded of silicone rubber;
   b) said body having a passage therein extending substantially along the length of said body and adapted to receive the tube segment;
   c) said body being split along at least a substantial portion of its length to form an upper leg and a lower leg which are joined together at corresponding one ends by a bridge and are separable at corresponding other ends;
   d) a base surface on said lower leg for seating against a patient;
   e) said passage being generally L-shaped and including a long segment extending generally longitudinally of said body and a short segment extending generally perpendicular to said long segment;
   f) one of said upper and lower legs having an annular collar formed therein adjacent its other end, said annular collar including a lip under which said other end of the other of said legs is nested;
   g) said passage extending through said annular collar;
   h) said body having an annular depression formed around it for receiving an O-ring; and
   i) a removable O-ring adapted to seat in said depression and normally hold said legs flush against each other in order to retain a tube segment in said passage.

* * * * *